United States Patent [19]

Bleisteiner et al.

[11] 4,300,905
[45] Nov. 17, 1981

[54] RAPID TEST FOR ASCORBIC ACID DETERMINATION

[75] Inventors: Manfred Bleisteiner; Walter Rittersdorf; Hans Wielinger, all of Mannheim, Fed. Rep. of Germany

[73] Assignee: Boehringer Mannheim GmbH, Mannheim, Fed. Rep. of Germany

[21] Appl. No.: 150,377

[22] Filed: May 15, 1980

[30] Foreign Application Priority Data

Jun. 28, 1979 [DE] Fed. Rep. of Germany ....... 2926068

[51] Int. Cl.$^3$ ............................................. G01N 33/82
[52] U.S. Cl. .................................... 23/230 B; 23/904; 23/932; 252/408; 422/56
[58] Field of Search ..................... 23/230 B, 904, 932; 422/56; 252/408

[56] References Cited

U.S. PATENT DOCUMENTS 3,771,964 11/1973 Fader ............................... 252/408 X
3,825,411 7/1974 Morin ................................ 23/230 B

OTHER PUBLICATIONS

The Merck Index–8th Edition, Merck & Co., Rahway, N.J., 1968, p. 640.

*Primary Examiner*—Arnold Turk
*Attorney, Agent, or Firm*—Sprung, Felfe, Horn, Lynch & Kramer

[57] ABSTRACT

Compositions and methods for rapidly determining ascorbic acid in aqueous solutions, consisting of an absorbent carrier containing 2,18-phosphomolybdic acid, an aliphatic hydroxycarboxylic acid buffer to adjust the test to pH 2.5 to 5.0, and an alkali chlorate; process for the preparation of such tests.

15 Claims, No Drawings

RAPID TEST FOR ASCORBIC ACID DETERMINATION

The present invention relates to a stable rapid test for the semiquantitative determination of ascorbic acid in beverages and body fluids.

Especially in seasons of the year when many weather induced respiratory diseases appear, high doses of vitamin C are given for therapeutic and prophylactic purposes. The quantities of ascorbic acid that are not metabolized in the body are excreted, principally in the urine; in this process concentrations of 20 mg/dl, and more, can be observed. 20 mg/dl for urine is about the concentration limit, from which point the test reactions for other parameters that are important for diagnosis, such as, for example, glucose, blood, etc., are so severly upset by ascorbic acid that a wrong diagnosis cannot be ruled out. It is, therefore, of great importance to the physician to be accurately informed of the presence and quantity of this reducing and interfering substance.

In the beverage industry, too, it is important to know how much ascorbic acid is contained in fruit juices, wines, etc. The vitamin C content is occasionally an essential criterion of the quality of the product.

Various wet chemical processes for the determination of ascorbic acid are known (*Rompps Chemie-Lexikon*, 7th ed., Franckh'sche Verlagsbuchhandlung, Stuttgart 1972, p. 3385), which, for example, are based on the reduction of certain dyes (decolorization of dichlorophenol indophenol, Tillman's reagent, methylene blue, iodine), use the chromatographic behavior in the thin-film or paper chromatogram, or make use of special reactions, such as dehydration to dehydroascorbic acid and its conversion into colored osazone with 2,4-dinitrophenyl hydrazine.

Because of the apparatus and time that are needed, the wet chemical processes have not always proved themselves, and are being displaced by rapid tests, especially for qualitative and semiquantitative tests.

The rapid tests for the determination of ascorbic acid that have become known so far are fundamentally based on two procedures already familiar from wet chemistry:

(a) the decolorization of certain dyes by reduction (German Publ. Specification 28 34 743 or U.S. Pat. No. 4,141,688);

(b) the production of a coloration by the reduction of phosphomolybdates to molybdenum blue (German Pat. No. 2309 794 or U.S. Pat. No. 3,771,964).

Rapid tests that are based on a decolorization reaction have the disadvantage, in principle, that reproducible test results are only obtained when the dye is exactly measured out and absolutely stabile. It is clear that the production of reproducible charges of such test-strips make considerable demands on manufacture and quality control. Furthermore, these tests have the disadvantage that the relatively largest changes in concentration in the lower range of concentration of the substrate produce the relatively smallest changes in concentration of the dye.

A rapid test that is based on the reduction of ammonium phosphomolybdate is described in *Spot Tests In Org. Analysis*, 1960, p. 405. The test has not proved itself in practice, however, since on the one hand, it must be prepared by means of a cumbersome double impregnation, and on the other hand, it is stable for only a few days. In addition, it is necessary to acidify the samples before the investigation, since in a neutral or alkaline medium, the test is disturbed by other substances.

As an improvement on this test, a rapid test is proposed in German patent application No. 2 309 794, consisting of a mixture of 2,18- and 2,24-phosphomolybdic acid, a neutral nitrate, and an organic acid, preferably malonic acid. This rapid test, usable in itself, however, still has the following disadvantages:

The use of a mixture of two chemically very similar heteropoly-acids makes considerable demands on quality control;

The preferred malonic acid and many other organic acids have the property, upon rather long storage in a closed vessel even at room temperature, of partly sublimating out of the test range. This results in other test ranges being negatively influenced in combination test strips during storage and transportation. Thus, for example, a pH-indication is falsified by the corresponding test paper.

The problem existed, therefore, of developing a rapid test for ascorbic acid that does not show the disadvantages mentioned above; i.e., which is based on the tested principle of coloration;

determines ascorbic acid in fruit juices (20–300 mg%) and in body fluids (0–50 mg%) equally well;

is simple and inexpensive in preparation and quality control; and is suitable for use in multiple tests, too, especially together with a pH-test.

Surprisingly, it has turned out that rapid tests in accordance with the problems posed above are obtained, which react with bright blue, well graduated colors, if the following components are used:

an alkali salt of 2,18-phosphomolybdic acid;

an aliphatic hydroxycarboxylic acid, if necessary, in a mixture with its alkali salt;

an alkali chlorate.

The alkali salts of 2,18-phosphomolybdic acid are well known compounds (A. Rosenheim and S. Traube, *Z. anorg. Chem.*, 65, 96–101 (1910)). It is understood that aliphatic hydroxycarboxylic acids are those containing one or more OH groups along with one or more —COOH groups in the molecule. It was established that such compounds, even with rather long storage in a closed vessel, do not sublimate to influence other test areas. Especially preferred hydroxycarboxylic acids are the commercial, inexpensive malic, citric, and tartaric acids. The alkali chlorates are also familiar, commercial compounds. The alkali chlorate serves to stabilize the test papers, since it prevents bluing by reducing constituents of the paper during storage. It must be considered surprising that the strong oxidizing agent chlorate, indeed, prevents the reduction of the molybdates during storage, but does not influence the analogous reduction by ascorbic acid in the test.

The test papers according to the present invention, for example, are prepared according to the following:

The alkali salt of 2,18-phosphomolybdic acid, in a concentration of 3.0–9.0 g/l is dissolved together with 2.0–6.0 g/l of alkali chlorate and 10–90 g/l of an aliphatic hydroxycarboxylic acid in water, with or without the addition of any organic solvent preferred that is miscible with water or of a lower alcohol. The solution is brought to a pH of 2.5–5.0 with an alkali liquor; such as lithium hydroxide, sodium hydroxide, etc.

Of course, one can also proceed in such a way that a mixture of hydroxycarboxylic acid and the corresponding alkali salt are used, while the mixing proportion is selected in such a way that a pH-value for the impregnating solution of 2.5–5.0 is obtained. Mixtures of the above named acids may also be used. Filter papers are impregnated, according to the usual procedure, with the impregnating solution prepared in this way. After drying, the test papers are cut, and by pasting them onto a handle of plastic foil, for example, or covering them with a thin net according to German Pat. No. 2 118 455, they are further processed into single-test or combination-test strips. With the test papers prepared in this way, the ascorbic acid content in liquids can be determined either with the aid of color comparison charts or with a remission photometric procedure.

The present invention is explained in detail by means of the following examples:

EXAMPLE 1

7 grams of the sodium salt of 2,18-phosphomolybdic acid, 4 grams of sodium chlorate, 40 grams of citric acid, and 13.5 grams of trilithium citrate are dissolved in a mixture of 600 ml of methanol and 380 ml of water. A filter paper, for example Type 2668, made by the Schleicher & Schüll Company, is impregnated with this solution, which has a pH-value of 3.6, and is dried for 1 hour at 60° C. Pieces measuring 6×6 mm are cut from the test paper prepared in this way, and sealed between a plastic handle and a thin nylon net, according to German Pat. No. 2 118 455. In urines with ascorbic acid in the important decision range of 0–40 mg of ascorbic acid/dl of urine, these test strips give very graduated reaction colors from bright greenish-blue to dark bluish-violet.

The test paper prepared in this way is also suitable for semiquantitative determination of ascorbic acid in fruit juices or other drinks, in which case, dilution with water may be necessary before the final determination. An objective evaluation of the reaction colors can be undertaken with commercial remission photometers. In the following table, the remission values measured with spectrophotometer DMR 21, using the Zeiss attachment ZR 21, are compared with the discolorations recognizable with the naked eye.

| Concentration of ascorbic acid mg % | % Remission at λ640 nm | Reaction color |
| --- | --- | --- |
| 0 | 89 | pale yellow |
| 5 | 36 | bright green |
| 10 | 26 | greenish-blue |
| 20 | 19 | blue |
| 40 | 12 | bluish-violet |
| 100 | 8 | dark bluish-violet |

EXAMPLE 2

6.5 grams of the sodium salt of 2,18-phosphomolybdenic acid, 4 grams of sodium chlorate, and 45 grams of malic acid or tartaric acid are dissolved in water, and adjusted with 10 n sodium hydroxide to pH-values between 2.5 and 5.0. Further processing into a test takes place as described in Example 1. The function and properties of the test strips correspond to those of the product described in Example 1.

EXAMPLE 3

A reaction paper according to Example 1 or Example 2, together with reaction papers for the determination of nitrite, pH-value, glucose, and ketone bodies, which were prepared according to familiar procedures, was processed into multiple test strips by covering it with a thin net. These multi-test strips were stored for several weeks in sealed tubes.

As comparison tests, reaction papers were prepared according to Example 1, in which the composition was changed so that instead of citric acid and lithium citrate, the same quantities of succinic acid or malonic acid and lithium hydroxide were used to adjust the pH to 3.6. As described above, these test papers were processed for multiple tests, and also stored for several weeks.

If the pH-value of urine, for example, is tested with a multiple test strip that contains the test for ascorbic acid in accordance with the present invention, the right pH-value is found. If the testing is done with multiple test strips that contain an ascorbic acid test paper that was prepared with succinic acid or malonic acid, an acid pH-value turns up.

The same negative influence on the pH-paper can be observed, if a test paper that has been impregnated with sodium-2-phospho-18-molybdate/sodium phospho-12-molybdate/sodium nitrate and malonic acid, according to German Pat. No. 2 309 794, is processed into multiple test strips and these are stored for several weeks.

It will be understood that the specification and examples are illustrative, but not limitative of the present invention and that other embodiments within the spirit and scope of the invention will suggest themselves to those skilled in the art.

What is claimed is:

1. Rapid test device for the determination of ascorbic acid consisting of an absorbent carrier impregnated with a phosphomolybdate selected from alkali salts of 2,18-phosphomolybdic acid, an organic acid selected from aliphatic hydroxycarboxylic acids, and an alkali chlorate said device exhibiting a pH value of 2.5 to 5 when moistened with water.

2. Rapid test device as claimed in claim 1 wherein said acid is at least one of the group consisting of malic acid, citric acid, or tartaric acid, and mixtures of these acids with their alkali salts.

3. Rapid test device as claimed in claim 1 wherein said acid is malic acid.

4. Rapid test device as claimed in claim 1 wherein said acid is citric acid.

5. Rapid test device as claimed in claim 1 wherein said acid is tartaric acid.

6. Rapid test device as claimed in claim 1 wherein said absorbent carrier is impregnated with an aqueous solution of
   3.0–9.0 g/l of the alkali salt of 2,18-phosphomolybdic acid;
   10.0–90.0 g/l of hydroxycarboxylic acid and its alkali salt;
   3.0–6.0 g/l of alkali chlorate and sufficient alkali hydroxide to adjust the pH value to 2.5 to 5.0.

7. Process for the preparation of a rapid test device as claimed in claim 1 which process comprises impregnating an absorbent carrier with an aqueous solution of
   3.0–9.0 g/l of the alkali salt of 2,18-phosphomolybdic acid;
   10.0–90.0 g/l of hydroxycarboxylic acid and it alkali salt;
   3.0–6.0 g/l of alkali chlorate and
   sufficient alkali hydroxide to adjust the pH value to 2.5 to 5.0 and drying the carrier.

8. Process as claimed in claim 7 wherein said aqueous solution also contains a water-miscible solvent.

9. Process as claimed in claim 8 wherein said solvent is a lower alcohol.

10. Method for determining ascorbic acid in a liquid, which method comprises contacting a liquid sample with a rapid test device as claimed in claim 1.

11. Method as claimed in claim 10 wherein said liquid is a body fluid.

12. Method as claimed in claim 11 wherein said body fluid is urine.

13. Method as claimed in claim 10 wherein said liquid is a beverage.

14. Method as claimed in claim 13, wherein said beverage is a fruit juice.

15. Method as claimed in claim 13 wherein said beverage is a wine.

* * * * *